United States Patent [19]

Fukushima et al.

[11] Patent Number: 5,667,762
[45] Date of Patent: Sep. 16, 1997

[54] METHOD FOR PREVENTING ADHESION OF THALLIUM 201 TO CONTAINER

[75] Inventors: Makoto Fukushima; Kazuhiro Kimura, both of Hyogo; Hirohiko Yamauchi; Kenichi Morishita, both of Chiba; Keietsu Takahashi, Hyogo, all of Japan

[73] Assignee: Nihon Medi-Physics Co., Ltd., Hyogo, Japan

[21] Appl. No.: 630,531

[22] Filed: Apr. 10, 1996

Related U.S. Application Data

[62] Division of Ser. No. 202,214, Feb. 25, 1994, abandoned.

[30] Foreign Application Priority Data

Mar. 5, 1993 [JP] Japan ................... 5-045104

[51] Int. Cl.$^6$ ................... A61K 51/12
[52] U.S. Cl. ................... 424/1.11; 424/1.61; 424/1.65; 514/917
[58] Field of Search ................... 424/1.11, 1.61, 424/1.65; 514/917; 423/2; 510/110; 252/625; 250/496.1

[56] References Cited

U.S. PATENT DOCUMENTS

| | | | |
|---|---|---|---|
| 4,425,319 | 1/1984 | Yokoyama et al. | 424/1.1 |
| 4,510,125 | 4/1985 | Grogg et al. | 424/1.1 |
| 4,645,660 | 2/1987 | Takahashi et al. | 424/1.1 |
| 4,888,163 | 12/1989 | Kubodera et al. | 424/1.1 |

FOREIGN PATENT DOCUMENTS 123314   10/1984   European Pat. Off. .

OTHER PUBLICATIONS

Kayfus, G.P., et al, Journal of Radionanalytical Chemistry vol. 68, No. 1–2, 269–276, 1982.
Langunas-Solar, M.C., et al, Int. J. Appl. Radiat. Isot., 33, 1439–1443, 1982.
Malinin, A.B., et al, Int. J. Appl. Radiat. Isot., 35, No. 7, 685–687, 1984.
Kozlova, M.D., et al, Int. J. Appl. Radiat. Isot., 38, No. 12, 1090–1091, 1987.
de Britto, J.L.Q. et al, J. Radioanal. Nucl. Chem., Letters 96/2/ 181–186, 1985.
Coursey, B.M., et al, Appl. Radiat. Isot., 41, No. 3, 289–291, 1990.
de Bruine, J.F., et al, Journal of Nuclear Medicine, vol. 26, No. 8, 925–930 (Aug. 1985).
Elliott, A.T., et al, Nulear Medicine Communications, vol. 11, No. 5, 375–381 (May 1990).
Reynolds, J.E.F., et al., Eds., Martindale –The Extra Pharmacopoeia, 28th edition, The Pharmaceutical Press, London, GB, pp. 1653–1657, & 1281–1293 (1982).

*Primary Examiner*—Gary E. Hollinden
*Assistant Examiner*—Michael G. Hartley

[57] ABSTRACT

There is disclosed an agent for preventing the adhesion of thallium 201 to a container which comprises a reducing substance as an active ingredient. There is also disclosed a radioactive diagnostic agent wherein the adhesion of thallium 201 to a container is prevented which comprises thallium 201 and a reducing substance.

7 Claims, No Drawings

METHOD FOR PREVENTING ADHESION OF THALLIUM 201 TO CONTAINER

This is a divisional of application Ser. No. 08/202,214 filed on Feb. 25, 1994, now abandoned.

FIELD OF THE INVENTION

The present invention relates to an agent which prevents thallium 201 from adhering to a container and a radioactive diagnostic agent containing thallium 201 wherein the adhering of thallium 201 to a container is prevented.

BACKGROUND OF THE INVENTION

Although thallium is a metal belonging to III-A group in the periodic table, it is known that, when it is in a certain ionic form, it takes the similar behaviors in the living body to those of potassium belonging to I-A group. In the normal myocardia, potassium ions are actively incorporated in the myocardial cells by an enzyme in the myocardial cell membranes and thereby are accumulated in the myocardia. This incorporation in the normal myocardia depends mainly upon the local blood flow in the myocardia. When a pharmaceutical agent containing thallium ions which is taking the similar behaviors to those of potassium ions in the body is injected intravenously, the agent becomes distributed to the muscles in the whole body. However, many thallium ions are distributed to the active myocardia but not in the affected parts such as ischemia and the like.

On the other hand, thallium ions are distributed depending upon the blood flow as in the case of cesium ions and as the result thallium ions have the marked tendency to be pooled in the tumor lesions in comparison with other tissues. This accumulation of thallium ions in the tumor lesions is presumed to be caused by substitution of potassium ions with thallium ions present in an enzyme. In addition, the extent of accumulation of thallium ions is largely influenced by the blood flow distribution toward the tumor.

In addition, thallium forms a complex with a certain compound, for example, diethyldithiocarbamate. As the result, the charge of the complex becomes neutral. This fact and high lipophilicity of the complex allow it to easily pass through the blood brain barrier and to be held in the brain over a sufficient period of time.

From the above descriptions, a solution of thallium 201 salt, in particular, thallium[$^{201}$Tl]chloride is useful as a radioactive diagnostic agent which is intravenously injected for examining the cardiac disorders and thyroid gland and lung tumors. And a complex of thallium 201 with a certain compound is useful as a radioactive diagnostic agent which is intravenously injected for diagnosing the brain disorders.

Such the radioactive diagnostic agent containing thallium [$^{201}$Tl]chloride for intravenous administration is prepared generally by diluting thallium[$^{201}$Tl]chloride with a physiological saline to the desired concentration of the radioactivity and filling the resulting solution in a container such as glass vial and syringe vial according to the preparation manner of the injectable solution on the Minimum Requirements for Radiopharmaceuticals in Japan. Thallium[$^{201}$Tl] chloride is prepared by irradiating protons accelerated by the cyclotron to thallium 203 or 205, isolating the generated lead 201 and collecting thallium 201 generated by the radioactive disintegration of lead 201.

OBJECTS OF THE INVENTION

A radioactive diagnostic agent containing thallium[$^{201}$Tl] chloride for intravenous administration is withdrawn from a glass vial into an injector upon use or is directly administered to a patient in the case of the syringe vial. In those cases, a nuclide of thallium 201 is observed to be adhered to a container of the vial. This adhered nuclide is difficult to be completely washed away from the container with an aqueous solvent such as physiological saline, hydrochloric acid and the like or a non-aqueous solvent such as diethyl ether. Since the adhered amount is sometimes over 10% of the filled radioactivity, the content of thallium 201 must be increased more or less in order to compensate the loss caused by the adhesion. On the other hand, the special counterplan needs to be considered for the disposal of the used vial and the problems of the irradiation.

Therefore, one object of the present invention is to provide an agent which can prevent thallium 201 from adhering to a container.

Another object of the present invention is to provide a radioactive diagnostic agent wherein the adhesion of thallium 201 to a container is prevented.

These object as well as other objects and advantages of the present invention will become apparent to those skilled in the art from the following description.

SUMMARY OF THE INVENTION

The present inventors studied extensively in order to prevent the adhesion of thallium 201 to a container. As the result, we found that the adhesion of thallium 201 to a container of glass vial, syringe vial and so on can be remarkably inhibited without losing the nuclear medicinal usefulness of the nuclide and lowering the radiochemical purity thereof by adding a reducing substance to the solution containing thallium 201. That is, in a thallium 201 solution containing a reducing substance, the chemical purity of thallium 201 is maintained high without undergoing the influences by the reducing substance and thallium-201 is rapidly accumulated in the myocardial cells or the tumor cells by intravenously injecting the solution. Furthermore, the adhesion of the radioactivity to a container where a thallium 201 solution has been withdrawn is hardly observed and the special counterplan does not need to be considered for the disposal of the used container and the irradiation exposure of a worker.

The present invention was done based on the above findings and provides an agent for preventing the adhesion of thallium 201 to a container which comprises a reducing substance as an active ingredient. The present invention also provides a radioactive diagnostic agent wherein the adhesion of thallium 201 to a container is prevented which comprises thallium 201 and a reducing substance.

The term "adhesion" used herein means adhesion, attachment or adsorption.

In the present invention, by simply adding a reducing substance to a solution containing thallium 201, the adhesion of thallium 201 to a container which was observed previously can be completely inhibited and one does not need to consider the special counterplan for disposal of a container and the irradiation exposure of a worker. Furthermore, the inherent biological and chemical properties of the nuclide thallium 201 is not lost by the addition of a reducing substance and the properties as a radioactive medicinal diagnostic agent are held as they are in myocardial imaging, tumor imaging, regional cerebral blood flow imaging and so on.

DETAILED DESCRIPTION OF THE INVENTION

A thallium 201 solution in the present invention may be an aqueous solution, preferably, a physiological saline containing thallium 201 or a salt thereof such as thallium chloride or a complex thereof such as thallium-diethyldithiocarbamate. The concentration of thallium 201 in the solution is 37 to 185 MBq/ml, usually, 74 MBq/ml.

The reducing substance to be added to the above thallium 201 solution may be selected from the substances usually known as a reducing agent or antioxidant so that it has physiologically no adverse effects to the human body in the range of the amount and the concentration to be used. Specifically, there are dibutylhydroxytoluene, tocopherol, butylhydroxyanisole, propyl gallate, erythorbic acid, sodium erythorbate, citric acid, sodium citrate, tartaric acid, ascorbic acid, ascorbic stearic ester, ascorbic palmitic ester, sodium hydrogen sulfite, sodium benzoate, sodium edetate, sodium oxymethanesulfonate, sodium sulfite, magnesium silicate, tocopherol acetate, magnesium oxide, sorbitol, sodium bicarbonate, calcium carbonate, sodium pyrosulfite, acetic acid, propylene glycol, magnesium metasilicate aluminate, sodium metaphosphate, hydroxyquinoline sulfate, calcium hydrogen phosphate, hydroquinone, stannous chloride, ferrous chloride, sodium borohydride, lithium aluminium hydride, sodium hydrosulfite and the like. These reducing substances may be used alone or as a combination thereof such as that of citric acid and ascorbic acid or that of tocopherol and ascorbic acid. The amount to be used is sufficient to prevent the adhesion of thallium 201 to a container and has no adverse effects on the human body. The amount is usually in the range of the concentration of 1 ppb to 10 W/V %, preferably, 1 μmg/ml to 100 μg/ml.

The reducing substance may be added to a thallium 201 solution at any stage and desirably before the final sterile-filtration step in view of that the end product is a pharmaceutical. Usually, a thallium 201 solution is first prepared and an appropriate amount of the reducing substance is added thereto as it is or as a solution.

The prepared thallium 201 solution containing the reducing substance is filled in an appropriate container, for example, vial or syringe vial and is stored until use. The container is usually made of glass or synthetic resin.

The following Examples further illustrate the present invention in detail but are not to be construed to limit the scope thereof.

EXAMPLE 1

Influences of L-ascorbic acid on adhesion of thallium 201 to direct container

Each 1 ml of a L-ascorbic acid/saline solution prepared to the concentration of 0, 10, 50 μg/ml was added to 1 ml of a thallium[$^{201}$Tl]chloride radioactive diagnostic agent obtained by the conventional method and the resulting mixture was filled in a syringe vial to obtain a radioactive diagnostic agent of thallium[$^{201}$Tl]chloride containing L-ascorbic acid. The all above operations were carried out under sterile conditions.

The radioactive diagnostic agent thus obtained was found to meet the thallium[$^{201}$Tl]chloride injections standard test of Japanese Pharmacopoeia. The radioactive diagnostic agent was allowed to stand for two days in the dark places and was subjected to the standard test again to be found to meet it.

For the radioactive diagnostic agent after standing, the radioactivity thereof was measured accurately as a whole of syringe vial, the solution contained therein was then drained from the syringe vial, the interior of the syringe vial was washed with a physiological saline, which was drained from the syringe vial and the radioactivity of this syringe vial was accurately measured again. Thereafter, the rate of thallium 201 adhered to the syringe vial was calculated according to the following equation.

$$A=(B/C)\times 100$$

wherein:

A=Rate of thallium 201 adhered to a syringe vial (%)

B=Radioactivity of a syringe vial after washing (MBq)

C=Radioactivity of a syringe vial containing therein a solution (MBq)

The results are shown in Table 1.

TABLE 1

| Influences of L-ascorbic acid on adhesion of thallium 201 to direct container | |
|---|---|
| Concentration of added L-ascorbic acid | Rate* of thallium 201 adhered to direct container |
| 0 μg/ml | 8.21% |
| 10 μg/ml | 1.06% |
| 50 μg/ml | 0.51% |

*the average (n = 3)

As shown in Table 1, by adding L-ascorbic acid to a thallium[$^{201}$Tl]chloride radioactive diagnostic agent, the rate of thallium 201 adhered to a direct container was remarkably decreased from 8.21% to 0.51%. And the adsorption rate was decreased with the concentration of L-ascorbic acid/saline.

From the above results, it was confirmed that the addition of L-ascorbic acid to a thallium[$^{201}$Tl]chloride radioactive diagnostic agent obtained by the conventional method decreases the adhesion of thallium 201 to a direct container while complying with the standard of Japanese Pharmacopoeia.

EXAMPLE 2

Influences of sodium sulfite on adhesion of thallium 201 to direct container

According to the same manners as those in Example 1, a thallium[$^{201}$Tl]chloride radioactive diagnostic agent containing sodium sulfite was prepared using a sodium sulfite/saline solution prepared to the concentration of 0, 10, 100 μg/ml.

The resulting radioactive diagnostic agent was found to meet the thallium[$^{201}$Tl]chloride injections standard test of Japanese Pharmacopoeia. The radioactive diagnostic agent was allowed to stand for two days in the dark places and was subjected to the standard test to be found to meet it.

After standing, the rate of thallium 201 adhered to a direct container was calculated according the same manners as those in Example 1. The results are shown in Table 2.

TABLE 2

| Influences of sodium sulfite on adhesion of thallium 201 to direct container | |
|---|---|
| Concentration of added sodium sulfite | Rate* of thallium 201 adhered to direct container |
| 0 μg/ml | 8.21% |
| 10 μg/ml | 1.14% |
| 100 μg/ml | 0.86% |

*the average (n = 3)

As shown in Table 2, by adding sodium sulfite to a thallium[$^{201}$Tl]chloride radioactive diagnostic agent, the rate of thallium 201 adhered to a direct container was remarkably decreased from 8.21% to 0.86% and the adhesion rate was decreased with the concentration of a sodium sulfite/saline solution.

From the above results, it was confirmed that, by adding sodium sulfite to a thallium[$^{201}$Tl]chloride radioactive diagnostic agent, the adhesion of thallium 201 to a direct container was decreased while complying with the standard of Japanese Pharmacopoeia.

EXAMPLE 3

Influences of hydroquinone on adhesion of thallium 201 to direct container

According to the same manners as those in Example 1, a thallium[$^{201}$Tl]chloride radioactive diagnostic agent containing hydroquinone was prepared using a hydroquinone/saline solution prepared to the concentration of 0, 10, 100 µg/ml.

The radioactive diagnostic agent thus obtained was found to meet the thallium[$^{201}$Tl]chloride injections standard test of Japanese Pharmacopoeia. The radioactive diagnostic agent was allowed to stand for two days in the dark places and was subjected to the standard test again to be found to meet it.

After standing, the rate of thallium 201 adhered to a direct container was calculated according to the same manners as those in Example 1. The results are shown in Table 3.

TABLE 3

Influences of hydroquinone on adhesion of thallium 201 to direct container

| Concentration of added hydroquinone | Rate* of thallium 201 adhered to direct container |
| --- | --- |
| 0 µg/ml | 8.21% |
| 10 µg/ml | 0.09% |
| 100 µg/ml | 0.07% |

*the average (n = 3)

As shown in Table 3, by adding hydroquinone to a thallium[$^{201}$Tl]chloride radioactive diagnostic agent, the rate of thallium 201 adhered to a direct container was remarkably decreased from 8.21% to 0.07%. And the adhesion rate was decreased with the concentration of a hydroquinone/saline solution.

From the above results, it was confirmed that, by adding hydroquinone to a thallium[$^{201}$Tl]chloride radioactive diagnostic agent obtained by the conventional method, the rate of thallium 201 adhered to a direct container was decreased while complying with the standard of Japanese Pharmacopoeia.

EXAMPLE 4

Influences of ferrous chloride on adhesion of thallium 201 to direct container

According to the same manners as those in Example 1, a thallium[$^{201}$Tl]chloride radioactive diagnostic agent is prepared using a ferrous chloride/saline solution.

After standing for two days, the radioactive diagnostic agent thus prepared meets the thallium[$^{201}$Tl]chloride injections standard test of Japanese Pharmacopoeia and thallium 201 contained therein is not adhered to a direct container.

EXAMPLE 5

Biodistribution of thallium[$^{201}$Tl]chloride radioactive diagnostic agent containing hydroquinone and Japanese Pharmacopoeia thallium[$^{201}$Tl]chloride injections in rats Each 0.1 ml of a thallium[$^{201}$Tl]chloride radioactive diagnostic agent (1 ml of the agent containing about 7 µg hydroquinone) and Japanese Pharmacopoeia thallium[$^{201}$Tl] chloride injection prepared according to the same manners as those in Example 3 was administered to the anesthetized female SD rats, weighing 162 to 204 g, 8 weeks old, via the tail vein. At 0.25, 3, 24, 48 and 72 hours after administration, the rats were sacrificed by bleeding from the descending vein, if necessary, under anesthetization. After sacrifice, the appropriate organs were isolated and the excreted urine and feces were also collected. The radioactivity in the organs, blood, urine, feces and the residual whole body was measured and the biodistribution rate (distribution rate in the body) was calculated.

The biodistribution results in rats which received a thallium[$^{201}$Tl]chloride radioactive diagnostic agent containing hydroquinone are shown in Table 4. The biodistribution results in rats which received a Japanese Pharmacopoeia thallium[$^{201}$Tl]chloride injection are shown in Table 5.

TABLE 4

Biodistribution results for thallium[$^{201}$]chloride radioactive diagnostic agent containing hydroquinone in rats (% dose/organ)

| Organ | Time after administration/hr | | | | |
| --- | --- | --- | --- | --- | --- |
| | 0.25 | 3 | 24 | 48 | 72 |
| Whole blood | 2.0 ± 0.4 | 0.9 ± 0.1 | 0.7 ± 0.2 | 0.4 ± 0.1 | 0.3 ± 0.0 |
| Heart | 2.9 ± 0.1 | 0.9 ± 0.1 | 0.5 ± 0.0 | 0.4 ± 0.0 | 0.3 ± 0.1 |
| Liver | 8.4 ± 0.2 | 6.5 ± 1.9 | 4.4 ± 0.7 | 2.7 ± 0.6 | 2.5 ± 0.5 |
| Lung | 1.8 ± 0.1 | 0.7 ± 0.1 | 0.4 ± 0.0 | 0.3 ± 0.0 | 0.3 ± 0.1 |
| Spleen | 0.9 ± 0.1 | 0.4 ± 0.0 | 0.2 ± 0.0 | 0.2 ± 0.0 | 0.1 ± 0.0 |
| Stomach | 1.4 ± 0.2 | 1.1 ± 0.2 | 0.9 ± 0.1 | 0.6 ± 0.1 | 0.4 ± 0.1 |
| Small intestine | 11.9 ± 0.6 | 14.6 ± 2.2 | 5.1 ± 0.6 | 3.6 ± 0.3 | 2.8 ± 0.4 |
| Large intestine | 4.5 ± 0.7 | 5.4 ± 1.0 | 14.8 ± 3.6 | 9.9 ± 4.1 | 3.8 ± 1.5 |
| Kidney | 13.1 ± 1.6 | 13.2 ± 1.1 | 9.4 ± 1.8 | 6.5 ± 0.6 | 5.9 ± 1.5 |
| Gonad | 0.3 ± 0.0 | 0.1 ± 0.0 | 0.1 ± 0.0 | 0.1 ± 0.0 | 0.0 ± 0.0 |
| Rest whole body | 53.7 ± 1.2 | 55.9 ± 1.2 | 54.1 ± 3.8 | 51.2 ± 2.2 | 42.5 ± 2.9 |
| Urine | 0.1 ± 0.1 | 0.9 ± 0.2 | 5.7 ± 0.6 | 10.2 ± 0.6 | 12.2 ± 1.4 |
| Feces | 0.0 ± 0.0 | 0.0 ± 0.0 | 4.2 ± 3.4 | 14.0 ± 6.8 | 28.9 ± 5.0 |

The values represent the means ± standard deviation in three rats.

TABLE 5

Biodistribution results for Japanese Pharmacopoeia thallium[$^{201}$Tl]chloride injection in rats (% dose/organ)

| Organ | Time after administration/hr | | | | |
|---|---|---|---|---|---|
| | 0.25 | 3 | 24 | 48 | 72 |
| Whole blood | 1.7 ± 0.2 | 1.0 ± 0.1 | 0.7 ± 0.1 | 0.4 ± 0.1 | 0.3 ± 0.1 |
| Heart | 3.0 ± 0.5 | 0.9 ± 0.0 | 0.5 ± 0.0 | 0.4 ± 0.1 | 0.3 ± 0.0 |
| Liver | 9.7 ± 1.6 | 6.7 ± 1.3 | 4.1 ± 0.4 | 3.2 ± 0.2 | 2.5 ± 0.3 |
| Lung | 1.9 ± 0.4 | 0.6 ± 0.1 | 0.3 ± 0.0 | 0.3 ± 0.0 | 0.2 ± 0.0 |
| Spleen | 0.9 ± 0.1 | 0.3 ± 0.1 | 0.1 ± 0.0 | 0.2 ± 0.0 | 0.1 ± 0.0 |
| Stomach | 1.2 ± 0.2 | 1.3 ± 0.1 | 0.8 ± 0.0 | 0.6 ± 0.1 | 0.4 ± 0.0 |
| Small intestine | 14.2 ± 0.6 | 11.7 ± 0.8 | 4.4 ± 0.2 | 3.4 ± 0.2 | 2.6 ± 0.2 |
| Large intestine | 4.0 ± 0.2 | 4.9 ± 0.8 | 12.0 ± 2.0 | 6.4 ± 3.8 | 4.4 ± 1.2 |
| Kidney | 12.9 ± 0.8 | 12.6 ± 0.3 | 8.8 ± 2.4 | 6.1 ± 0.2 | 4.8 ± 0.6 |
| Gonad | 0.3 ± 0.0 | 0.1 ± 0.0 | 0.1 ± 0.0 | 0.0 ± 0.0 | 0.0 ± 0.0 |
| Rest whole body | 51.0 ± 2.1 | 59.7 ± 1.4 | 50.2 ± 4.5 | 50.9 ± 4.5 | 39.1 ± 3.4 |
| Urine | 0.1 ± 0.0 | 0.6 ± 0.3 | 8.4 ± 1.2 | 9.1 ± 1.9 | 12.6 ± 3.1 |
| Feces | 0.0 ± 0.0 | 0.0 ± 0.0 | 9.9 ± 4.4 | 19.2 ± 5.1 | 32.7 ± 4.5 |

The values represent the mean ± standard deviation in three rats.

As shown in Tables 4 and 5, the uptake of the radioactivity in the heart (myocardia) which is the base of medicinal usefulness is about 3.0% at 0.25 hour after administration in both formulations and no differences in excretion pattern of the radioactivity were found between them. In addition, no significant differences were found in the biodistribution and excretion pattern of the radioactivity among other organs.

From the above results, it was confirmed that the addition of hydroquinone to a Japanese Pharmacopoeia thallium [$^{201}$Tl]chloride injection has no influences on the biodistribution of thallium 201 in animals.

EXAMPLE 6

Prevention of adhesion of thallium 201 to direct container in thallium[$^{201}$Tl]diethyldithiocarbamate solution A thallium[$^{201}$Tl]diethyldithiocarbamate complex which is prepared according to the method by J. F. de Bruine et al. (see J. Nucl. Med. 26: 925–930, 1985) is known to decompose in a solution and, as the result of decomposition, thallium[$^{201}$Tl]ions are produced. This causes the adhesion of thallium 201 to a direct container. However, the adhesion of thallium 201 to a direct container can be prevented only by adding a L-ascorbic acid/physiological saline solution (concentration: 100 μg/ml) to a thallium[$^{201}$Tl] diethyldithiocarbamate solution.

What is claimed is:

1. A method of preventing thallium-201 in a composition comprising thallium-201 or salt or complex thereof from adhering to a container therefor comprising including in admixture with the thallium-201, salt or complex in the container a reducing substance in amount effective to decrease the amount of thallium-201 adhering to the container upon dispensing of the contents.

2. The method according to claim 1, wherein the thallium-201 or salt or complex thereof is selected from the group consisting of thallium[$^{201}$Tl]chloride and thallium[$^{201}$Tl] diethyldithiocarbamate.

3. The method according to claim 2, wherein the thallium-201 or salt or complex thereof is thallium[$^{201}$Tl]chloride.

4. The method according to claim 2, wherein the thallium-201 or salt or complex thereof is thallium[$^{201}$Tl] diethyldithiocarbamate.

5. The method according to claim 3, wherein the reducing substance is selected from the group consisting of dibutylhydroxytoluene, tocopherol, butylhydroxyanisole, propyl gallate, erythorbic acid, sodium erythorbate, citric acid, sodium citrate, tartaric acid, ascorbic acid, ascorbic stearic ester, ascorbic palmitic ester, sodium hydrogen sulfite, sodium benzoate, sodium edetate, sodium oxymethanesulfonate, sodium sulfite, magnesium silicate, tocopherol acetate, magnesium oxide, sorbitol, sodium bicarbonate, calcium carbonate, sodium pyrosulfite, acetic acid, propylene glycol, magnesium metasilicate aluminate, sodium metaphosphate, hydroxyquinoline sulfate, calcium hydrogen phosphate, hydroquinoline, stannous chloride, ferrous chloride, sodium borohydride, lithium aluminum hydride, sodium hydrosulfite and combination thereof.

6. The method according to claim 3, wherein the reducing substance is selected from the group consisting of sodium sulfite, hydroquinone, ferrous chloride and combination thereof.

7. The method according to claim 3, wherein the reducing substance is L-ascorbic acid.

* * * * *